United States Patent [19]
Alaluf et al.

[11] Patent Number: 6,042,841
[45] Date of Patent: Mar. 28, 2000

[54] COSMETIC METHOD OF TREATING SKIN

[75] Inventors: Simon Alaluf; Karen Elizabeth Barrett; Martin Richard Green, all of Bedford, United Kingdom; Karen Angela Ottey, Vlaardingen, Netherlands; Anthony Vincent Rawlings, Bedford, United Kingdom

[73] Assignee: Unilever Home & Personal Care USA Division of Conopco, Inc., Greenwich, Conn.

[21] Appl. No.: 09/268,284

[22] Filed: Mar. 15, 1999

[30]     Foreign Application Priority Data

Mar. 16, 1998 [GB] United Kingdom ............... 9805564
Dec. 22, 1998 [EP] European Pat. Off. ........... 98310626
Dec. 22, 1998 [EP] European Pat. Off. ........... 98310627

[51] Int. Cl.$^7$ ........................................ A61K 7/48
[52] U.S. Cl. .................. 424/401; 514/506; 514/553; 514/554; 514/557; 514/558; 514/844
[58] Field of Search ............... 424/401; 514/506, 514/512, 553, 554, 557, 558, 844

[56]             References Cited

U.S. PATENT DOCUMENTS

| | | | |
|---|---|---|---|
| 4,966,754 | 10/1990 | Purohit et al. | 424/195.1 |
| 5,380,894 | 1/1995 | Burg et al. | 554/219 |
| 5,422,371 | 6/1995 | Liao et al. | 514/560 |
| 5,516,793 | 5/1996 | Duffy | 514/474 |
| 5,558,871 | 9/1996 | Griat et al. | 424/401 |
| 5,679,374 | 10/1997 | Fanchon et al. | 424/450 |
| 5,733,572 | 3/1998 | Unger et al. | 424/450 |
| 5,807,820 | 9/1998 | Elias | 514/11 |
| 5,866,040 | 2/1999 | Nakama et al. | 252/312 |

FOREIGN PATENT DOCUMENTS

| | | |
|---|---|---|
| 116 439 | 8/1984 | European Pat. Off. . |
| 355 842 | 2/1990 | European Pat. Off. . |
| 631 772 | 1/1995 | European Pat. Off. . |
| 709 084 | 8/1995 | European Pat. Off. . |
| 888 773 | 1/1999 | European Pat. Off. . |
| 98/16104 | 4/1998 | WIPO . |
| 09/38278 | 9/1998 | WIPO . |
| 98/40461 | 9/1998 | WIPO . |
| 98/53698 | 12/1998 | WIPO . |

OTHER PUBLICATIONS

Derwent abstract of RU 2027440 (1995).
Derwent abstract of CS 245821 (1986).
Afifi et al., "Some Pharmacological Activities of Essential Oils of Certain Umbelliferous Fruits", Vet. Med. J. Giza., vol. 42, No. 3 pp. 85–92 (1994).
Yagaloff et al., "Essential Fatty Acids are Antagonists of the Leukotriene $B_4$ Receptor", Prostaglandins Leukotrienes and Essential Fatty Acids, 52, pp. 293–297 (1995).
Devchand et al., "The PPARα–leukotriene $B_4$ pathway to inflammation control", Nature, vol. 384, pp. 39–43 (1996).
Keller et al., "Fatty acids and retinoids control lipid metabolism through activation of peroxisome proliferator–activated receptor–retinoid X receptor heterodimers", Proc. Natl. Acad. Sci. USA 90, pp. 2160–2164 (1993).
Chemical Abstract, vol 87, No. 24, Dec. 12, 1977, Columbus, Ohio, US, No. 87:189308s.
Derwent abstract of De 197 03 745 (1997).
Derwent abstract of EP 248 701 (1987).

*Primary Examiner*—Michael A. Williamson
*Attorney, Agent, or Firm*—Rimma Mitelman

[57]             ABSTRACT

A cosmetic method for treating aged, wrinkled and/or photodamaged skin is provided through topical application of a composition which comprises petroselinic acid and/or derivatives thereof. The method also reduces skin irritation and also lightens the color of skin.

1 Claim, No Drawings

COSMETIC METHOD OF TREATING SKIN

This invention relates to a cosmetic method of improving the condition and appearance of skin and to the use of petroselinic acid in the preparation of topical compositions for improving the condition and appearance of skin.

Skin is subject to deterioration through dermatological disorders, environmental abuse (wind, air conditioning, central heating) or through the normal aging process (chronoaging) which may be accelerated by exposure of skin to sun (photoaging). In recent years the demand for cosmetic compositions and cosmetic methods for improving the appearance and condition of skin has grown enormously.

Consumers are increasingly seeking "anti-aging" cosmetic products which treat or delay the visible signs of chronoaging and photoaging skin such as wrinkles, lines, sagging, hyperpigmentation and age spots.

Consumers also frequently seek other benefits from cosmetic products in addition to anti-aging. The concept of "sensitive skin" has also raised the consumer demand for cosmetic products which improve the appearance and condition of sensitive, dry and/or flaky skin and to soothe red, and/or irritated skin. Consumers also desire cosmetic products which treat spots, pimples, blemishes etc.

Many people are concerned with the degree of pigmentation of their skin. For example, people with age spots or freckles may wish such pigmented spots to be less pronounced. Others may wish to reduce the skin darkening caused by exposure to sunlight or to lighten their natural skin colour. To meet this need many attempts have been made to develop products that reduce the pigment production in the melanocytes. However, the substances thusfar identified tend to have undesirable side effects, e.g. skin irritation.

Consequently such substances are not suitable for cosmetic use or they can only be applied at a concentration at which their skin lightening effect is less than desired. Using a combination of different skin lightening substances may be considered to reduce adverse side effects but there is a substantial risk that by using such a combination the skin lightening is reduced as well due to competition effects. Therefore there is a need for improvement in the effectiveness of cosmetic skin lightening products particularly, such that they do not irritate the skin.

The use of fatty acids, including petroselinic acid, in cosmetic formulations for treating the hair are known. EP-A-116439) describes hair tonics which include fatty acids (such as petroselinic acid) for alleviating dandruff and itch and for stimulating hair growth.

EP-A 709084 describes the use of coriander seed oil, which is rich in petroselinic acid triglycerides, in a cosmetic composition for moisturising dry skin conditions.

We have now surprisingly found further undisclosed properties of petroselinic acid, which are useful in cosmetic compositions for topical application to skin to provide previously undisclosed skin care benefits.

We have now found that effective treatment and prevention of normal skin conditions due to chronoaging or photoaging, such as wrinkles, lines, sagging, hyperpigmentation and age spots, may be obtained through the application of cosmetic compositions to the skin which comprise petroselinic acid or derivatives thereof. We have also found that the use of petroselinic acid in cosmetic compositions advantageously provides further skin benefits in addition to anti-aging such as for soothing sensitive and/or irritated skin and for lightening the skin.

SUMMARY OF THE INVENTION

According to a first aspect of the present invention there is provided a cosmetic method of providing at least one skin care benefit selected from: treating/preventing wrinkling, sagging, aged and/or photodamaged skin; boosting collagen deposition in skin, boosting decorin production in skin, enhancing tissue repair; lightening skin; soothing irritated, red and/or sensitive skin; improving skin texture, smoothness and/or firmness; the method comprising applying to the skin a topical composition comprising petroselinic acid and/or derivatives thereof.

The present invention also encompasses the use of petroselinic acid and/or derivatives thereof in a topical composition for providing at least one skin care benefit selected from treating/preventing wrinkling, sagging, aged and/or photodamaged skin; boosting collagen deposition in skin, boosting decorin production in skin, enhancing tissue repair; lightening skin; soothing irritated, red and/or sensitive skin; improving skin texture, smoothness and/or firmness.

The inventive methods and use of petroselinic acid thus provide anti-aging benefits which result in the promotion of smooth and supple skin with improved elasticity and a reduced or delayed appearance of wrinkles and aged skin, with improved skin colour. A general improvement in the appearance, texture and condition, in particular with respect to the radiance, clarity, and general youthful appearance of skin is achieved. The inventive methods and uses are also beneficial for soothing and calming sensitive and/or irritated skin. Petroselinic acid is also useful for topical application to human skin for reducing melanin production and thus lightening the skin on which it has been applied. Thus the inventive methods advantageously provide a wide range of skin care benefits.

The term "treating" as used herein includes within its scope reducing, delaying and/or preventing the above mentioned skin conditions such as wrinkled, aged, photodamaged, and/or irritated skin and generally enhancing the quality of skin and improving its appearance and texture by preventing or reducing wrinkling and increasing flexibility, firmness, smoothness, suppleness and elasticity of the skin. The cosmetic methods and the uses of petroselinic acid and/or derivatives according to the invention may be useful for treating skin which is already in a wrinkled, aged, photodamaged and irritated condition or for treating youthful skin to prevent or reduce those aforementioned deteriorative changes due to the normal aging/photo aging process.

DETAILED DESCRIPTION OF THE INVENTION

Petroselinic acid (hereinafter referred to as PA is a monounsaturated long chain (C18) fatty acid, having the formula $CH_3(CH_2)_{10}CH=CH(CH_2)_4COOH$.

The invention also includes derivatives of the free acid which thus comprise petroselinic acid moieties. Preferable derivatives include those derived from substitution of the carboxyl group of the acid, such as esters (eg retinyl esters, triglyceride esters, monoglyceride esters, diglyceride esters, phosphoesters), amides (eg ceramide derivatives), salts (eg alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of PA substituents on the glycerol backbone are included. The triglycerides must contain at least one PA moiety. For example, of the three esterifiable positions on the glycerol backbone, the 1 and 2 positions may be esterified with PA and by another lipid at position 3 or as an alternative, the glycerol backbone could be esterified by PA at the 1 and 3 positions with another lipid at position 2.

Oils that are rich in petroselinic acid triglyceride are thus also suitable for use in the present invention. Such oils are commercially available and include parsley seed oil, carrot seed oil, fennel fruit oil, parsnip seed oil, coriander seed oil, chervil seed oil, caraway plant oil, and celery seed oil.

Wherever the term "petroselinic acid" or "PA" is used in this specification it is to be understood that the derivatives thereof comprising PA moieties are also included. "PA moieties" refers to PA fatty acyl portion(s) of a PA derivative.

The active, petroselinic acid, to be employed in accordance with the present invention is present in the topical composition in an effective amount. Normally the total amount of the active is present in an amount between 0.0001% and 50% by weight of the composition. More preferably the amount is from 0.01% to 10% and most preferably from 0.1% to 5% in order to maximise benefits at a minimum cost.

Dermatological Acceptable Vehicle

The composition used according to the invention also comprises a dermatologically/cosmetically acceptable vehicle to act as a dilutant, dispersant or carrier for the active, PA. The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the active, PA, other specific skin-benefit actives such as sunscreens, other skin lightening agents, skin tanning agents may also be included. The vehicle may also further include adjuncts such as perfumes, opacifiers, preservatives, colourants and buffers.

Product Preparation, Form, Use and Packaging

To prepare the topical composition used in the method of the present invention, the usual manner for preparing skin care products may be employed. The active components are generally incorporated in a dermatologically acceptable carrier in conventional manner. The active components can suitably first be dissolved or dispersed in a portion of the water or another solvent or liquid to be incorporated in the composition. The preferred compositions are oil-in-water or water-in-oil emulsions.

The composition may be in the form of conventional skin-care products such as a cream, gel or lotion or the like. The composition can also be in the form of a so-called "wash-off" product e.g. a bath or shower gel, possibly containing a delivery system for the actives to promote adherence to the skin during rinsing. Most preferably the product is a "leave-on" product; a product to be applied to the skin without a deliberate rinsing step soon after its application to the skin.

The composition may packaged in any suitable manner such as in a jar, a bottle, tube, roll-ball, or the like, in the conventional manner.

The method of the present invention may be carried out one or more times daily to the skin which requires treatment. The improvement in skin appearance will usually become visible after 3 to 6 months, depending on skin condition, the concentration of the active components used in the inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

In order that the present invention may be more readily understood, the following examples are given, by way of illustration only.

EXAMPLES

This example demonstrates the anti-aging benefits of petroselinic acid.

Example 1

Identification of Procollagen-I and Decorin Upregulation in Skin In Vivo Following Topical Retinoic Acid Treatment for Comparative Purposes Collagen, the predominant matrix skin protein is known to impart tensile strength to skin. Decorin is a proteoglycan which is known to be important for controlled and correct deposition of collagen in the extracellular matrix of skin. It is also known in the art that the levels of collagen and decorin in skin are significantly reduced with aged and/or photodamaged skin. Many studies have shown that the levels of collagen type I in skin is decreased with age and/or with increased photodamage, (for example Lavker, R. J. Inv. Derm., (1979), 73, 79–66; Griffiths et al. N. Eng. J. med. (1993) 329, 530–535). In the case of decorin, it has been shown that mRNA expression and expression of the proteoglycan is greatly reduced in photodamaged skin in vitro (Bernstein et al. Lab. Invest. (1995) 72, 662–669). The reduction of the levels of these skin proteins is accordingly associated with a decrease in the tensile strength of the skin causing wrinkles and laxity.

It is well known in the art that retinoic acid is a potent anti-aging active and induces dermal repair of photodamaged skin. It has been shown that wrinkle effacement and dermal repair following topical treatment of skin with retinoic acid arises through new collagen deposition and synthesis in the skin (for example, Griffiths et al. N. Eng. J. med. (1993) 329, 530–535). It is widely accepted that strengthening of the dermal matrix by boosting the level of collagen in skin using retinoic acid provides anti-aging/dermal repair benefits. Procollagen I is a precursor of collagen. Increased production of procollagen I in response to a test compound application is a marker of an increased collagen level.

Two groups of women were recruited with identical or nearly identical degrees of mild to moderate photodamage on each outer forearm. They were supplied with 0.05% retinoic acid in a moisturising base (Retinova®) and also with a colour matched moisturising cream with similar sensory characteristics (Dermacare® lotion), but no active ingredients, as a placebo control. Each participant of the two groups applied the Retinova® to one outer forearm and placebo (Dermacare®) to the other outer forearm. Group 1 applied the products daily to their outer forearms for 14 weeks and the Group 2 applied the products to their outer forearms for 28 weeks. At the end of the studies two full thickness 4 mm punch biopsies were taken from the treated areas of each forearm. Immunohistochemical analysis of the biopsy tissue taken from the participants was performed to identify the effect of retinoic acid treatment on the expression of the skin extracellular matrix components, decorin and procollagen-I, as compared with the placebo treated forearms. The following procedure was followed:

MATERIALS

Antibody dilution buffer for wax sections was composed of Tris Buffered Saline (TBS), 3% bovine serum albumin (BSA), 0.05% Triton X-100 and 0.05% sodium azide. Primary antibodies for procollagen-I (amino terminal) were obtained from Chemicon International Inc. (cat# MAB 1912, rat IgGl) and used on wax sections at a dilution of 1:800, overnight at 4° C. after the section had been pretreated with trypsin (0.5 mg/ml, 25 minutes, 37° C.). Primary antibodies for decorin were obtained from Biogenesis (rabbit polyclonal) and used on wax sections at a dilution of 1:800, overnight at 4° C. Anti-rat biotinylated secondary antibodies, obtained from DAKO (cat# E0468, rabbit polyclonal), were applied to wax sections at a dilution of 1:400. Anti-rabbit biotinylated secondary antibodies, obtained from Amersham (cat# RPN 1004, donkey polyclonal), were applied to wax sections at a dilution of 1:400. Streptavidin conjugated alkaline phosphatase, obtained from Zymed (cat# 43-4322), was used at a concentration of 1:2500. Fast Red chromogen was obtained from DAKO (cat# K597). Gills #3 Haematoxylin nuclear counterstain obtained from Sigma (cat# GHS-3), was filtered and used without dilution. Trypsin was obtained from Sigma (cat# T-7186) and slides were mounted with Glycergel from DAKO (cat# C563).

METHODS

Wax sections of the biopsy tissue were mounted on silane coated slides and baked for 18 hours at 55° C. The slides were dewaxed through xylene and alcohol and brought to water and then transferred to TBS. DAKO® pen was used to ring the sections. The sections were processed for antigen retrieval using trypsin where necessary, as indicated for each antibody. Where antigen retrieval was necessary, the slides were incubated for 25 minutes at 35° C. with trypsin at 0.5 mg/ml (Sigma Cat # T-7186). The protease was subsequently rinsed off (2×2 minutes) with TBS. Following antigen retrieval, if necessary, or otherwise directly after ringing the sections, non specific antibody binding was blocked with 5% solutions of secondary antibody host serum in TBS/0.5% BSA/0.1% sodium azide as the blocking solution for at least 20 mins at room temperature in a humid chamber. The excess blocking solution was drained off, but the sections were not allowed to dry. The sections were then incubated with the primary antibody (appropriately diluted as indicated above) in a humid chamber overnight at 4° C. Antibody was subsequently drained from the sections, without allowing them to dry. The slides were then washed with TBS to remove unbound primary antibody—a one minute rinse followed by three five minute washes—and then incubated with the appropriate secondary antibody (appropriately diluted as indicated above) in a humid chamber for 1 hour at room temperature. The antibody solution was subsequently drained from the slides without allowing the section to dry. The slides were washed in TBS, a one minute rinse followed by 4×5 min washes, in order to remove the unbound secondary antibody. For the biotinylated secondary antibody the sections were subsequently incubated with streptavidin conjugate for 45 mins at 37° C. and then washed in TBS to remove unbound streptavidin conjugate. The chromogen was added and the colour developed with observation to avoid over-staining. The sections were then counterstained and mounted.

Differences in the expression of procollagen-I and decorin between retionoic acid (Retinova®) and placebo (Dermacare®) treated sites were determined by visual assessment of the immunohistochemically stained sections using light microscopy.

This analysis identified marked upregulation of both procollagen-I and decorin in the photodamaged skin following topical application of retinoic acid (Retinova®), as set out in Table 1 below.

TABLE 1

Effect of Retinoic Acid Treatment on Expression of Procollagen I and Decorin in Skin In Vivo

|  | Total No. of Participants | No. of Participants showing marked increase in expression of procollagen-I | No. of Participants showing marked increase in expression of decorin |
| --- | --- | --- | --- |
| Group 1 after 14 weeks | 16 | 9 | 10 |
| Group 2 after 28 weeks | 15 | 10 | 15 |

The extra cellular matrix components procollagen 1 and decorin are thus clearly identifiable markers of retinoic acid induced dermal repair.

Procedure for Measuring Procollagen-I and Decorin Synthesis in Human Dermal Fibroblasts

Preparation of Dermal Fibroblast Conditioned Medium

Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Dot Blot Assay for Procollagen-I and Decorin Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm² flask and maintained in serum free DMEM as described above. Assay samples were subsequently applied in triplicate to a prewetted sheet of Immobilon-P transfer membrane using the 96-well Bio-Dot Apparatus from Bio-Rad as described in the manufacturers guidelines. Approximately 200 μl of medium was applied per well. The medium was allowed to filter through the membrane under gravity (30 minutes) after which the membrane was washed twice with PBS (200 μl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) BSA/0.1% (v/v) Tween 20 in PBS, whilst those for procollagen-I analysis were blocked with 5% (w/v) non fat dried milk powder/ 0.05% Tween 20 in PBS. The following day, the membranes were probed with 1:10000 dilution of primary antibodies to either human procollagen-I (MAB1912; rat monoclonal; Chemicon Int. Inc., Temecula, Calif.) or human decorin (rabbit polyclonal; Biogenesis) for 2 hours at room temperature. The membranes were subsequently washed with TBS/ 0.05% Tween 20 (3×5 minutes) and then incubated with 1:1000 dilution of $^{125}$I-conjugated anti-rat or anti-rabbit F(ab')2 fragments (Amersham) as required for 1 hour at room temperature. Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin and procollagen-I synthesis were determined relative to a vehicle treated control value of 100 arbitrary units.

TESTS

The table 2 below indicates the effects of petroselinic acid on procollagen-I and decorin synthesis in human dermal fibroblasts, and the amounts in which it was applied. In order to normalise the results the effects of the test substance was determined relative to a vehicle treated control value of 100 arbitrary units. For comparison, a trial was performed with retinoic acid to assess its effect on decorin synthesis in human dermal fibroblasts. The concentrations of reagents used in the trials had no influence on cell viability.

TABLE 2

The Effect on Procollagen-I and Decorin Synthesis by Petroselinic Acid

| Treatment | Procollagen-I | Decorin |
|---|---|---|
| Control (Vehicle) | 100 | 100 |
| Petroselinic Acid (10 μM) | 118.4 ± 8.6 (n = 3) | 153.0 ± 19.1 (p = 0.01, n = 4) |

The results in table 2 indicate that petroselinic acid significantly upregulates the synthesis of both procollagen-I and decorin in human dermal fibroblasts as compared to the control.

The level of decorin in skin is associated with improved condition and appearance of skin. Increasing the level of decorin in skin is important for controlled and correct deposition of collagen in skin which is associated with many skin benefits such as wrinkle effacement and dermal repair of photodamaged skin.

The comparative trial with retinoic acid (1 μm) showed an upregluation of decorin, 138±14.0 (p=0.035, n=4), as determined relative to a vehicle treated control value of 100 arbitrary units. Surprisingly, the data thus further indicates that the magnitude of the upregulation of and decorin synthesis in human dermal fibroblasts effected by petroselinic exceeds that of the bench-mark anti-aging dermal repair active, retinoic acid.

Example 2

This example measures the anti-irritancy functionality of petroselinic acid.

Keratinocyte SDS Viability Assay

Methodology

Keratinocytes were grown in 96 well plates to approximately 80% confluency in keratinocyte growth medium (KGM) which was then replaced with KGM without hydrocortisone for 24–48 hours. The cells were then treated with a concentration of sodium dodecyl sulphate (SDS) which will produce cell viability of approximately 50% (2μ/ml) in the presence or absence of petroselinic acid. The cells were then dosed with petroselinic acid at concentrations indicated in table 3 below. The control did not contain any SDS or test compounds. After incubating for 24 hours the medium was removed and the viability determined by the Neutral Red method. With this method the cells were incubated for 3 hours in KGM containing 25 μg/ml neutral red after which the medium was removed and the cells were then extracted with 1 ml of 1% (v/v) acetic acid, 50% (v/v) ethanol for 30 min units. The absorbance of the extract at 562 nm was determined and the viability evaluated by reference to control wells which contained neither SDS nor test compounds. The results that were obtained are summarised in table 3 below:

TABLE 3

| TREATMENT | | Keratinocyte viability | | |
|---|---|---|---|---|
| SDS μg/ml | PA μM | % of control Mean | SD | n |
| 0 | 0 | 100 | 11.9 | 8 |
| 2 | 0 | 55.8 | 18.3 | 8 |
| 2 | 0.1 | 94.5 | 16.5 | 8 |
| 2 | 1.0 | 84.1 | 16.8 | 8 |
| 2 | 10 | 85.8 | 11.9 | 8 |

All petroselinic acid (PA) values show significantly increased viability compared to the 2 μg/ml SDS value alone as determined by 1 way ANOVA with Student-Neumann-Kuels multiple comparison, p<0.05.

This methodology has shown that the keratinocyte toxicity of an irritant relates to the irritancy effect of the agent in vivo (Lawrence, J N, Starkey, S., Dickson, F M & Benford, D J. Use of human and rat keratinocyte cultures to assess skin irritation potential. Toxicol. In Vitro. 10, 331–340 (1996).) Thus here we show that treatment with petroselinic acid significantly reduces the toxic effects of SDS on keratinocytes and accordingly that it has an anti-irritant functionality.

Example 3

This example demonstrates that petroselinic acid can effectively reduce the basal levels of $PGE_2$ (prostaglandin $E_2$) secreted by keratinocytes in vitro.

Keratinocyte $PGE_2$ Assay

Keratinocytes were grown in 96 well plates to approximately 80% confluency in keratinocyte growth medium (KGM). This was then replaced with KGM without hydrocortisone for 24–48 hours. The cells were then dosed with petroselinic acid in amounts shown in table 4 below. No petroselinic acid was added to the control cells. The cells were incubated with (or, for the control, without) petroselinic acid for 24 hours. At the end of the incubation the medium was harvested and assayed for the basal release of the pro-inflammatory $PGE_2$ by enzyme-linked immuno assay using a commercial $PGE_2$ kit (Amersham, Buckinghamshire, England).

The cells were then tested for viability by the neutral red up-take method described in example 2 above. Cell viability was not found to be adversely effected by treatment with petroselinic acid used at the concentrations tested.

The anti-inflammatory potential of the test compounds were assessed by the ability of the compounds to reduce the basal levels of secreted $PGE_2$ as compared to the control. Statistical significance was determined using the Student's t-test. The results that were obtained are summarised in Table 4 below.

TABLE 4

| Treatment | Keratinocyte $PGE_2$ Levels pg/well Mean | SD | n |
|---|---|---|---|
| Control | 197.9 | 50.2 | 4 |
| PA 0.1 µM | 150.1 | 55.7 | 4 |
| PA 1 µM | 117.8 | 22.6 | 4 |

Statistical analysis using 1 way ANOVA with Student-Neumann-Kuels multiple comparison demonstrated that at 0.1 and 1 µM petroselinic acid (PA) significantly ($p<0.05$) reduced the release of $PGE_2$ from unstimulated keratinocytes.

$PGE_2$ is a well known mediator of inflammation in the skin see Greaves et al "Prostagludus, leukotriemes, phospholipase, platelet actuating factor and cytokines: an integrated approach to inflammation of human skin", Arch. Dermatol. Res. (1988) 280 [Supp]: 533–541.

The results indicate that petroselinic acid treated keratinocytes produce less of the pro-inflammatory prostaglandin $PGE_2$ thereby reducing the inflammatory potential of the skin.

Example 4

This example measures the effect of petroselinic acid on reducing the inflammatory response of dermal fibroblasts.

Fibroblasts $PGE_2$ and ICAM Assay

Intracellular adhesion molecules (ICAM) and $PEG_2$ production by human skin fibroblasts can be induced by the inflammatory stimulus PMA (phorbal myristate acetate). PMA represents an external stressor which induces oxidative stress and inflammatory responses in cells. This model is used to model inflammation in vivo.

Primary human foreskin fibroblasts at passage 2 (P2) were seeded into 96-well plates at 10000 cells/well and maintained for 24 hours in an atmosphere of 5% carbon dioxide in Dulbeccos Modified Eagles Medium (DMEM) supplemented with 10% foetal calf serum. Petroselinic acid was added to fresh cell media (DMEM, supplemented with 10% foetal calf serum) in dimethylsulphoxide (DMSO, final concentration 1%) in triplicate and incubated for a further 24 hours. Phorbal myristate acetate (PMA) (Sigma) was added to the media and the cells incubated for a further 24 hours. The control did not contain any test compounds nor any PMA. The fibroblasts/media were then analysed as described below immediately or snap frozen in liquid nitrogen and stored at $-70°$ C. for future analysis. The cells were then counted and data from the dot-blot analysis subsequently standardised to cell number.

Prostaglandin E2 ($PGE_2$) assay: Volumes of 50 µl culture medium were taken for $PGE_2$ assay after gently shaking the culture plate. $PGE_2$ levels in the medium were determined with a Biotrak $PGE_2$ immunoassay kit (Amersham, UK). The assay is based on the competition between unlabelled $PGE_2$ in the sample and a fixed quantity of horseradish peroxidase labelled $PGE_2$ for a limited amount of fixed $PGE_2$ specific antibody. Concentrations of unlabelled sample $PGE_2$ are determined according to a standard curve which was obtained at the same time.

ICAM-1 assay: Media were discarded and cells washed with Dulbecco PBS. To the washed cells, 150 µl 0.1% Triton X-100 (Sigma) was added for 3 minutes to extract ICAM from cell membrane. The extracts were transferred to Eppendoff centrifuge tubes and centrifuged at 1000 g for 2 min to remove cell debris. A volume of 100 µl supernatant was used for ICAM assay. The soluble ICAM-1 was assessed with commercially available immunoenzymometric assay kit (R&D Systems). Concentrations of ICAM-1 in the samples were determined based on parallelly running standard curve.

The results that were obtained from the $PGE_2$ and ICAM assay are summarised in table 5 below.

TABLE 5

Effects of Petroselinic Acid on PMA-Induced ICAM and $PGE_2$ Production in Human Skin Fibroblasts

| TREATMENT | N | ICAM (ng/ml) | $PGE_2$ (pg/ml) |
|---|---|---|---|
| Control | 4 | 3.07 ± 0.54 | 32 ± 6 |
| PMA (10 nM)-treated | 4 | 14.42 ± 1.86 | 2371 ± 241 |
| PMA + PA (0.1 uM) | 4 | 8.64 ± 0.89* | 500 ± 127* |
| PMA + PA (1 uM) | 4 | 7.71 ± 0.66* | 486 ± 93* |
| PMA + PA (10 uM) | 4 | 7.39 ± 0.14* | 233 ± 139* |
| PMA + PA (100 uM) | 4 | 6.68 ± 1.35* | 117 ± 39* |

* $p < 0.001$ compared with those of PMA-treated cells

The above results show that challenging cells with an inflammatory stimulus such as PMA (Phorbol myristyl acetate) causes an increase in the inflammatory response as measured by prostaglandin E2 ($PGE_2$) production. Petroselinic acid, even at the levels of 0.1 µm, dramatically reduces the inflammatory response as measured by $PGE_2$ production. The results thus demonstrates that petroselinic acid has good anti-inflammatory activity.

The above results also demonstrate that challenging cells with PMA causes an increase in ICAM production. Petroselinic acid decreases the production of Intracellular adhesion molecule (ICAM), which is another marker of inflammation. These results thus further demonstrate that petroselinic acid has good anti-inflammatory action.

Example 5

Skin Lightening Assay Methodology

Cell maintenance

B16-F1 mouse melanoma cells (American Type Culture Collection, Maryland, USA) were maintained in 75 cm$^2$ culture flasks in RPMI 1640 medium (ICN-Flow, cat. no. 12-60-54) supplemented with L-glutamine (4 mM) and 10% foetal bovine serum (FBS) at 37° C. in a water saturated, 5% $CO_2$ in air atmosphere. Cells were passaged twice weekly.

Pigmentation Assay

Subconfluent B16 cells were seeded in 96 well microtiter plates at a density of 5000 cells/well and cultured overnight in DMEM (Life Technologies, NY) containing 10% foetal bovine serum and 1% penicillin/streptomycin without phenol red at 37° C. under 5% CO2. After 24 hours, the media was replaced with fresh media containing the test materials or vehicle controls. Cells were incubated for 72 hours at which time melanin was visible in the control wells. Next, the melanin containing media from each well was transferred to a clean 96 well plate and quantified by reading the absorbance at 530 nm using a microplate spectrophotometer (Dynatech MR5000) and correcting for the baseline absorption of fresh medium. As the corrected absorption is proportional to the melanin concentration the percentage pigmentation for a skin lightening test substance can be calculated as:

% pigmentation=($OD_{530}$ test/$OD_{530}$ ref)×100% where $OD_{530}$ test and $OD_{530}$ ref indicate the average corrected absorption of the medium from the wells with the test substance and that of the medium from the wells without the test substance. The percentage inhibition caused by the test substance is then 100 - % pigmentation.

Cell viability assay

Melanin production may be reduced by inhibition of melanogenesis but it may also be affected by cytotoxicity or cell proliferation. To test whether this occurred cell viability was tested by neutral red dye absorption. Neutral red is a water soluble dye that passes through the intact plasma membrane and becomes concentrated in the lysosomes in intact cells.

Total neutral red dye uptake is proportional to the number of viable cells in culture.

Immediately following the removal of medium for melanin analysis from the microtitre wells, 200 μl fresh pre-warmed neutral red dye (ex. Sigma, UK, Cat. Nr 2889) at 25 μg/ml medium was applied to the cells and incubated for 3 hours as for cell maintenance. Dye which had not been taken up by the cells was removed by inversion of the plate and tapping on absorbent paper. The cells were washed with 200 μl PBS, which was then removed again. 100 μl solvent (50% $H_2O$, 49% ethanol, 1% acetic acid) was added. After 20 minutes at ambient temperature each plate was shaken for 5 seconds on a microtitre plate shaker. The absorption was measured as described above.

Tests

Table 6 below indicates the skin lightening test substances evaluated and the amount in which they were applied. The percentage inhibition of melanin production caused by the test substances as described above is reflected in the table as well.

Values less than 100% melanin control indicate inhibition of melanogenesis. Thus the results in Table 3 show that PA inhibits melanin production.

In the trials the test substance was diluted with DMEM in the amounts shown in table 5 below.

TABLE 6

| | Melanin in Media | | | Neutral Red Cell Viability | | |
|---|---|---|---|---|---|---|
| Treatment | % Control | S.D. | t-Test vs control | % Control | S.D. | t-Test vs control |
| Control | 100 | 8.5 | | 100.0 | 4.6 | |
| 0.1% Petroselinic Acid | 19.3 | 1.2 | ** (0.000) | 1.0 | 0.4 | ** (0.000) |
| 0.04% Petroselinic Acid | 3.9 | 0.7 | ** (0.000) | 69.9 | 8.8 | ** (0.000) |
| 0.02% Petroselinic Acid | 55.3 | 18.2 | ** (0.000) | 103.1 | 3.9 | ** (0.082) |
| 0.013% Petroselinic Acid | 40.4 | 10.7 | ** (0.000) | 105.2 | 4.1 | (0.006) |
| 0.01% Petroselinic Acid | 79.5 | 8.6 | ** (0.000) | 104.8 | 3.9 | * (0.009) |

Student's t-Test ** p < 0.01 * p < 0.05 (n = 4)

Example 6

The formulation below describes an oil in water cream suitable for the methods and uses according to the present invention. The percentages indicated are by weight of hte composition.

| | wt % |
|---|---|
| Mineral Oil | 4 |
| Petroselinic acid (triglyceride) | 1.15 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

Example 7

The formulation below describes an emulsion cream according to the present invention.

| FULL CHEMICAL NAME OR CTFA NAME | TRADE NAME | WT. % |
| --- | --- | --- |
| PA triglyceride | | 2.0 |
| disodium EDTA | Sequesterene Na2 | 0.05 |
| magnesium aluminium silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 250HHR | 0.5 |
| glycerine, USP | Glycerine USP | 2.0 |
| xanthan gum | Keltrol 1000 | 0.2 |
| triethanolamine | Triethanolamine (99%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18 DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | Myrj 59 | 2.0 |
| sodium stearoyl lactylate | Pationic SSL | 0.5 |
| hydroxycaprylic acid | Hydroxycaprylic Acid | 0.1 |
| retinyl palmitate | Vitamin A Palmitate | 0.06 |
| alpha-bisabolol | Alpha-bisabolol | 0.2 |
| water, DI | | q.s. to 100 |

Both the above topical compositions of example 6 and 7 provide an effective cosmetic treatment to lighten the colour of skin and/or to improve the appearance of wrinkled, aged, photodamaged, and/or irritated skin, when applied to skin that has deteriorated through the aging or photoaging or when applied to youthful skin to help prevent or delay such deteriorative changes. The compositions can be processed in conventional manner.

What is claimed is:

1. A cosmetic method of providing at least one skin care benefit selected from: treating wrinkling, sagging, aged and/or photodamaged skin; boosting collagen deposition in skin, boosting decorin production in skin, enhancing tissue repair; improving skin texture, smoothness and/or firmness; the method comprising applying to the skin a topical composition consisting essentially of petroselinic acid and derivatives thereof in an amount of 0.0001–50% by weight in a dermatologically/cosmetically acceptable vehicle.

* * * * *